US005653724A

United States Patent [19]

Imonti

[11] Patent Number: 5,653,724

[45] Date of Patent: Aug. 5, 1997

[54] ANGLED PHACOEMULSIFIER TIP

[76] Inventor: Maurice M. Imonti, 25707 Compass Way, San Juan Capistrano, Calif. 92675

[21] Appl. No.: 546,157

[22] Filed: Oct. 20, 1995

Related U.S. Application Data

[63] Continuation of Ser. No. 264,191, Jun. 22, 1994, abandoned , which is a continuation-in-part of Ser. No. 108,991, Aug. 18, 1993, abandoned .

[51] Int. Cl.[6] .......... A61B 17/32

[52] U.S. Cl. .......... 606/169; 606/107; 604/22

[58] Field of Search .......... 606/107, 169; 604/22

[56] References Cited

U.S. PATENT DOCUMENTS

| | | | |
|---|---|---|---|
| 3,942,519 | 3/1976 | Shock | 606/169 |
| 4,169,984 | 10/1979 | Parisi | 606/169 |
| 4,526,571 | 7/1985 | Wuchiwich | 604/22 |
| 4,561,438 | 12/1985 | Bonnet et al. | 604/22 |
| 4,570,632 | 2/1986 | Woods | 606/107 |
| 4,643,717 | 2/1987 | Cook et al. | 606/169 |
| 4,832,683 | 5/1989 | Idemoto et al. | 604/22 |
| 4,886,491 | 12/1989 | Parisi et al. | 604/22 |
| 4,911,161 | 3/1990 | Schechter | 606/107 |
| 4,974,581 | 12/1990 | Wiksell | 604/22 |
| 5,045,054 | 9/1991 | Hood et al. | 604/22 |
| 5,154,694 | 10/1992 | Kelman | 606/169 |
| 5,163,433 | 11/1992 | Kagawa et al. | 606/128 |
| 5,222,937 | 6/1993 | Kagawa | 606/169 |
| 5,254,082 | 10/1993 | Takase | 604/22 |
| 5,462,522 | 10/1995 | Sakurai et al. | 604/22 |

FOREIGN PATENT DOCUMENTS

| | | | |
|---|---|---|---|
| 514810 | 11/1992 | European Pat. Off. | 604/22 |
| 0993929 | 2/1983 | U.S.S.R. | 606/169 |
| 1438745 | 11/1988 | U.S.S.R. | 604/22 |
| 1572614 | 6/1990 | U.S.S.R. | 606/107 |
| 1695900 | 12/1991 | U.S.S.R. | 604/22 |
| 8602257 | 4/1986 | WIPO | 604/22 |

*Primary Examiner*—Michael Buiz
*Assistant Examiner*—Patrick W. Rasche
*Attorney, Agent, or Firm*—Michael G. Petit

[57] ABSTRACT

An aspiration/irrigation tip adapted for use with a handpiece for the removal of a cataractous lens from the eye is described. The tip, which may be used with an ultrasonic handpiece, is a bent, hollow-bore needle. The shaft of the needle is bent to form a distal invasive portion and a proximal non-invasive portion which attaches to the handpiece. The angle in the shaft enables the surgeon to hold the handpiece at an ergonomically preferred angle with respect to the eye while performing phacoemulsification. Heating of non-target tissues such as the cornea due to friction between the non-target tissue and the vibrating needle is reduced.

5 Claims, 1 Drawing Sheet

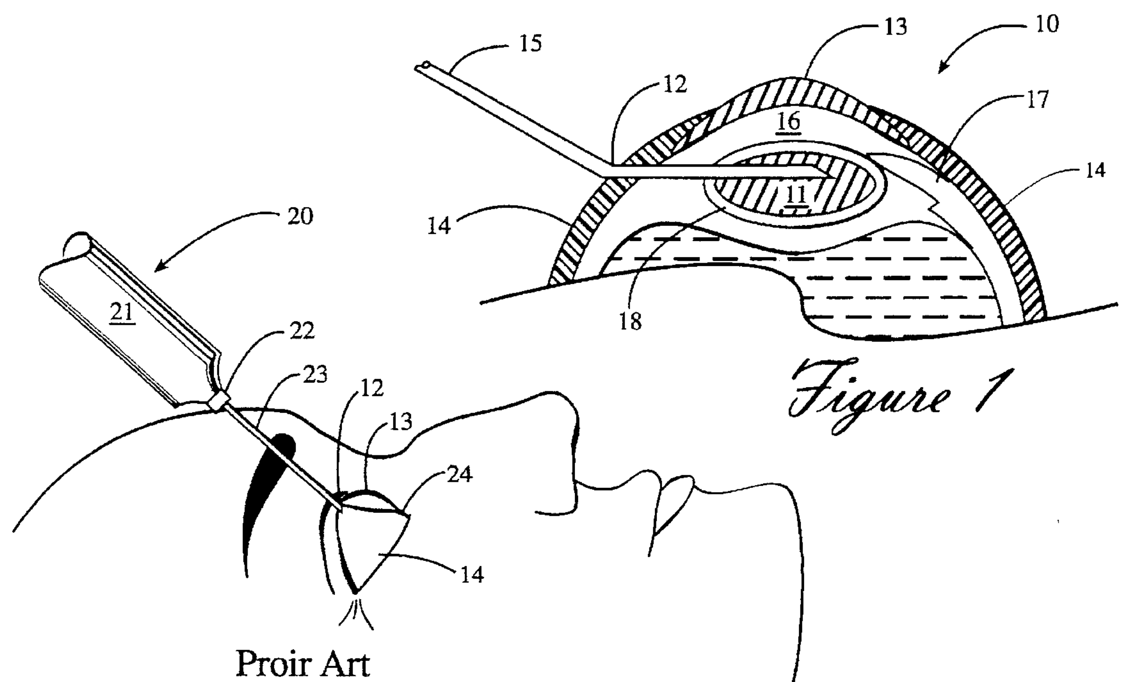
Figure 1
Figure 2
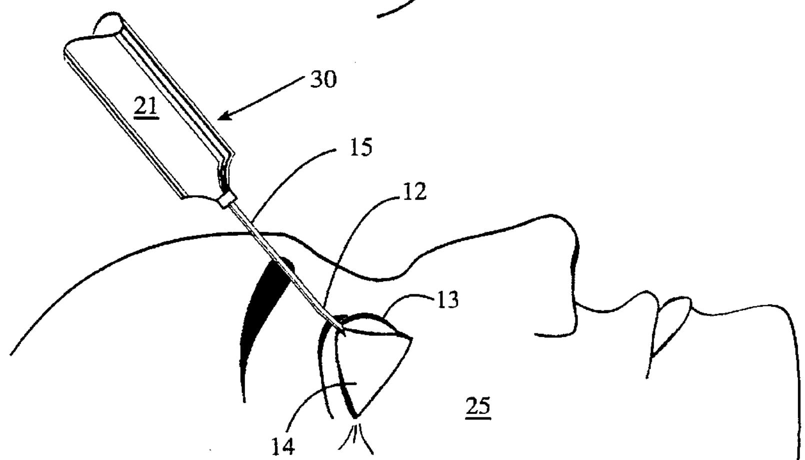
Figure 3
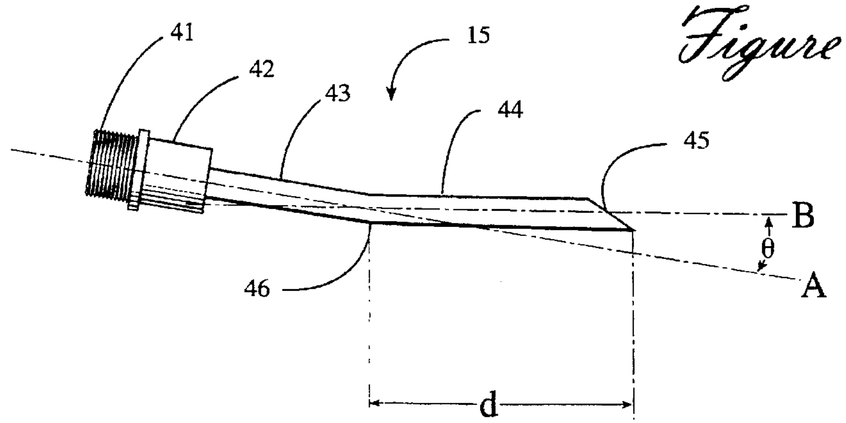
Figure 4

ANGLED PHACOEMULSIFIER TIP

CROSS REFERENCE TO RELATED APPLICATIONS

This is a continuation of application Ser. No. 08/264,191; filed Jun. 22, 1994 now abandoned which is a continuation in part of Ser. No. 08/108,991, filed Aug. 18, 1993 now abandoned.

BACKGROUND OF THE INVENTION

1. Field of the Invention

This invention relates to a surgical instrument which utilizes irrigation, aspiration and ultrasonic frequencies to disintegrate and remove a cataract lens from an eye and, more particularly, to a tip adapted for use with an irrigating/ultrasonic handpiece for insertion removing the lens/cortex of the eye.

2. Prior Art

An opaque or cloudy cataract lens must be replaced to restore vision. A technique for extracting the lens cortex from an eye known as phacoemulsification and aspiration has been developed by C. D. Kelman and A. Banko and described in U.S. Pat. No. 3,589,363. In this technique, an ultrasonic vibrating tip is inserted through a small corneal incision wherein the tip contacts the lens and disintegrates and emulsifies it with an irrigating fluid. A delivery tube coaxial with the tip provides a flow of saline into which the disintegrated lens readily disperses to form an emulsion. The emulsified lens tissue is then aspirated through a second channel in the tip and the lens is thereby removed.

Phacoemulsifier devices comprise a power supply, and, in combination, a handpiece and a tip portion. Typical of such handpiece and tip combinations are U.S. Pat. No. 4,040,414 to Suroff, U.S. Pat. No. 4,988,334 to Hornlein, et al., and U.S. Pat. No. 4,886,491 to Parisi, et al. Perhaps representative of the art in phacoemulsifier handpieces and tips is U.S. Pat. No. 5,162,044 to Gahn, et al., the contents of which are incorporated herein by reference. Gahn describes a phacoemulsification probe which uses ultrasonic frequencies to treat cataracts. His probe includes a rotatable handle to facilitate repositioning of the needle in the eye during surgery while maintaining a comfortable and secure grip on the instrument.

Gahn describes the general problems relating to comfortable grips. According to Gahn, the rotatable handle provides the surgeon with the degree of freedom needed for comfortable lens removable. There are however certain problems associated with the straight tips depicted in Ghan which were not discussed. Among these is the fact that the axis of the tip is coaxial with the axis of the handpiece and, due to projection of the eyebrow, the lens of the eye must be entered at an angle requiring repositioning of the needle tip to access the entire lens. Due to the fact that the prior art phacoemulsifier handpieces utilize a straight needle they are not ergonomic and are difficult to use. This, is turn makes it more difficult for surgeons to learn the phacoemulsification technique. Further, the straight tip increases the likelihood of wound enlargement which can result in loss of anterior chamber pressure, iris chafing and corneal burns. It is desirable to provide both a phacoemulsifier handpiece having irrigating and aspirating capabilities and an ultrasonic handpiece having irrigation and aspiration capabilities (alternatively referred to herein as an "I/A ultrasonic handpiece") with a tip comprising a needle wherein the needle is bent or angled so as to afford comfortable access to the lens of the eye through an incision in the eye.

SUMMARY OF THE INVENTION

It is, therefore, an object of this invention to provide a tip suitable for removal of the lens cortex of an eye adapted for use with an I/A ultrasonic handpiece.

It is yet another object of this invention to provide a tip for a phacoemulsification handpiece which is angled to provide a more comfortable ergonomic angle during phacoemulsification and lens cortex removal.

It is still another object of the invention to provide a tip for use with an ultrasonic phacoemulsification I/A handpiece that is capable of disintegrating and emulsifying the lens of an eye without the need for increased cavitation or use of high ultrasonic power.

These and other objects of the invention will soon become apparent as we turn now to the preferred embodiments.

BRIEF DESCRIPTION OF THE DRAWINGS

FIG. 1 is a fragmentary view showing a portion of the eye.

FIG. 2 is a perspective view of an irrigating and aspirating phacoemulsification device removing a lens cortex from the eye according to the prior art.

FIG. 3 is a perspective drawing of the tip of the present invention used with the prior art handpiece to remove the lens cortex of an eye.

FIG. 4 is a side view of the phacoemulsification irrigator/aspirator tip according to the present invention.

DESCRIPTION OF THE PREFERRED EMBODIMENT

Turning first to FIG. 1, when the natural crystalline lens 11, which is posterior to the anterior chamber 16 and iris 17 of the eye 10 becomes cloudy and opaque to the transmission of light, a cataract condition exists. In order to correct this impairment, the cataract lens 11 must be removed from the lens capsule 18 and replaced with an optically transparent element. The technique for lens removal usually requires an incision 12 at or near the junction of the cornea 13 and the sclera 14. It is through this incision 12 that the phacoemulsifier tip 15 is placed to access the anterior chamber 16 and lens 11.

FIG. 2 shows a patient 25 lying in a recumbent position with a prior art phacoemulsifier I/A ultrasonic handpiece 21 and tip 20 (alternatively referred to herein, in combination as a "phacoemulsifier probe") positioned for use. The handle 21 of the phacoemulsifier probe 20 must be elevated at an angle to the eye 23 so that the surgeon can hold the probe 20 comfortably. However, holding the handpiece at this angle tends to stress the tissue at the incision site. The phacoemulsifier handpiece 21 has a distal portion 22 to which a tip 23 comprising a hollow-bore phacoemulsifier needle is attached. The tip portion 23 is inserted through the incision 12 between the cornea 13 and sclera 14 and into the lens 11 (not shown in FIG. 2).

Turning now to FIG. 3, we see a phacoemulsifier probe 30 having the handpiece 21, but with a new angled tip 15. The angled tip 15, enables the surgeon to comfortably hold the phacoemulsifier handpiece 21 and introduce the angled tip 15 into the incision 12 between the sclera 14 and the cornea 13 to penetrate the lens while keeping the invasive portion of the tip in the plane of the lens. Consequently, the stress on the tissue at the incision site is reduced. In addition, the loading of the ultrasonic tip 15, due to wound friction is reduced requiring less ultrasonic power to fragment and emulsify the lens.

The actual construction of the needle 15 is shown in FIG. 4. The needle, is hollow-bore and preferably made from titanium, stainless steel or an aluminum/titanium alloy, has a threaded, non-invasive proximal end 41 which is adapted to matingly engage a receptacle (not shown) within the distal end 22 of the handpiece 21. There is a nut portion 42 which enables the facile connection of the needle or tip 15 to the handpiece 21. The tip 15 comprises a non-invasive portion 43 having a first axis "A" and an invasive angled portion 44 having a second axis "B". The distance d between the distal end 45 of the tip 15 and the position of the bend 46 in the tip 15 must be equal to or greater than the diameter of the lens 11.

Surprisingly, it has been found that the emulsification of the lens proceeds more efficiently if the bend 46 is not located at a vibrational node. The mass of the invasive angled portion 44 of the tip 15 is displaced laterally in an up and down as well as a longitudinal displacement motion which is transferred to the surrounding lens, avoiding undue stress at the bend. The ideal frequency range for the tip 15 is 38 KHz–48 KHz. For this frequency range and an overall tip length of 0.875 inches, the length d of the invasive portion 44 is preferably about 0.580 inches.

The angled phacoemulsifier tip made in accordance with the present invention offers particular advantages to the physician who is not yet highly skilled at phacoemulsification. This is because the invasive portion of the tip maintains a more parallel position with respect to the posterior capsule, reducing the risk of breaking the posterior capsule. The tip also offers ease of tip entry into the eye, a more comfortable hand position (thereby reducing fatigue) and easier access to the deep-set eye. The unitary construction of the tip, together with the positioning of the head at a non-nodal position, provides greater efficiency during phacoemulsification requiring less ultrasound power to be delivered to the eye. Use of the tip described herein provides a dramatic reduction in iris chafing due to the tip operating on a more parallel plane to the iris. The angle of the non-invasive portion to the invasive portion is preferably between 30° and 60°. Accordingly, three tips, having angles of 30°, 45° and 60° should suffice for most procedures.

The bent tip 15 allows easier insertion of the invasive portion 44 into the incision because of the angle θ of the axis of the invasive portion 44 of the tip 15 with respect to the axis A of the non-invasive portion 43 and the handpiece axis. Because the handpiece must be held at an angle with respect to the patient's forehead and eyebrow in order to access the lens, the angled tip 15 provides access to the entire plane of the lens of the eye through the incision 12. Moreover, with the bend in the tip, manipulation of the invasive portion 44 of the tip 15 within the anterior chamber 16 is easier. Furthermore, since the invasive portion of the tip is parallel to the posterior portion of the lens capsule 18, the angled tip reduces the possibility of damage to the posterior capsule during extraction of the lens cortex. The angle θ between the B axis and the A axis of the invasive and non-invasive portions of the tip respectively is preferably in the range of 5° through 85°.

Other tips are designed to cause cavitation within the lens and cortex. Such cavitation, comprising sequentially expanding/collapsing bubbles in the lens, is useful for disintegrating the lens but generates a good deal of heat and is difficult to control. The angled tip according to the present invention produces less heat when emulsifying the lens. This is due to reduction of the air bubbles being placed into the patient's eye. The angled portion 44 of the tip 15 acts as a barrier for air bubbles. Reducing air bubbles during the emulsification stage of the procedure is advantageous inasmuch as such bubbles can hamper visualization and prevent the surgeon from identifying the tissue being emulsified. Since more ultrasonic energy is being delivered to the end of the ultrasonic tip there is a greater efficiency in emulsifying the cataract.

The angled tip described herein has many advantages over the straight tips of the prior art. The ergonomic design of the angled tip permits the surgeon to perform the procedure with less fatigue. The angled tip of the present invention also permits easier access to deep set eyes. As previously stated, the greater efficiency of the angled tip due to reduced mechanical friction allows the surgeon to reduce the ultrasonic power being delivered to the eye which can dislodge and remove non-regenerative endothelial cells from the cornea. Reduced power also reduces the likelihood of corneal burns at the incision site.

While particular embodiments of the present invention have been illustrated and described, it would be obvious to those skilled in the art that various other changes and modifications can be made without departing from the spirit and scope of the invention. It is therefore, intended to cover in the appended claims all such changes and modifications that are within the scope of this invention.

What I claim is:

1. A surgical tip operable for conducting mechanical vibrations having a frequency between 38 KHz and 48 KHz from an ultrasonic phacoemulsifier handpiece to a tissue, said tip comprising a hollow elongate tubular member of unitary construction and having; (a) a straight non-invasive proximal portion with attachment means thereon, said attachment means being operable for releasably attaching said non-invasive proximal portion to said handpiece and having a length of 0.295 inches and a central first axis; and (b) an invasive distal portion comprising a straight, elongate, substantially cylindrical member terminating in a beveled distal tip and having an axial length of 0.580 inches and a second central axis; and (c) a bend between said proximal portion and said distal portion wherein said first and said second axis intersect at an angle between 10° and 15°.

2. The tip of claim 1 wherein said hollow tubular member is stainless steel.

3. The tip of claim 1 wherein said hollow tubular member is titanium.

4. The tip of claim 1 wherein one end of said invasive portion is beveled.

5. The tip of claim 1 further comprising means for delivering an irrigating fluid from said non-invasive portion to said invasive portion of said tip and a means for aspirating a fluid from said invasive portion of said tip to said non-invasive portion of said tip.

* * * * *